US00PP19471P2

(12) United States Plant Patent
Meilland

(10) Patent No.: US PP19,471 P2
(45) Date of Patent: Nov. 18, 2008

(54) HYBRID TEA ROSE PLANT NAMED 'MEIKATANA'

(50) Latin Name: *Rosa hybrida*
Varietal Denomination: Meikatana

(75) Inventor: Alain A. Meilland, Antibes (FR)

(73) Assignee: Meilland International S.A., Le Luc en Provence (FR)

( * ) Notice: Subject to any disclaimer, the term of this patent is extended or adjusted under 35 U.S.C. 154(b) by 0 days.

(21) Appl. No.: 12/000,623

(22) Filed: Dec. 14, 2007

(30) Foreign Application Priority Data

May 25, 2007 (QZ) ..... 2007/1164

(51) Int. Cl.
*A01H 5/00* (2006.01)

(52) U.S. Cl. ..... Plt./140

(58) Field of Classification Search ..... Plt./140
See application file for complete search history.

*Primary Examiner*—Kent L Bell
(74) *Attorney, Agent, or Firm*—Buchanan Ingersoll & Rooney PC

(57) ABSTRACT

A new and distinct variety of Hybrid Tea rose plant is provided that forms in abundance on a nearly continuous basis attractive large double very velvety blossoms that are dark red in coloration. The vegetation is glossy dark green and contrasts nicely with the blossom coloration. The plant develops well on its own roots. Also, the plant forces well and is particularly well suited for cut flower production under greenhouse growing conditions.

1 Drawing Sheet

Figures 1, 2, 3, 4, 5, 6, 7, 8, 9, 10, 11, 12, 13, 14, 15, 16:
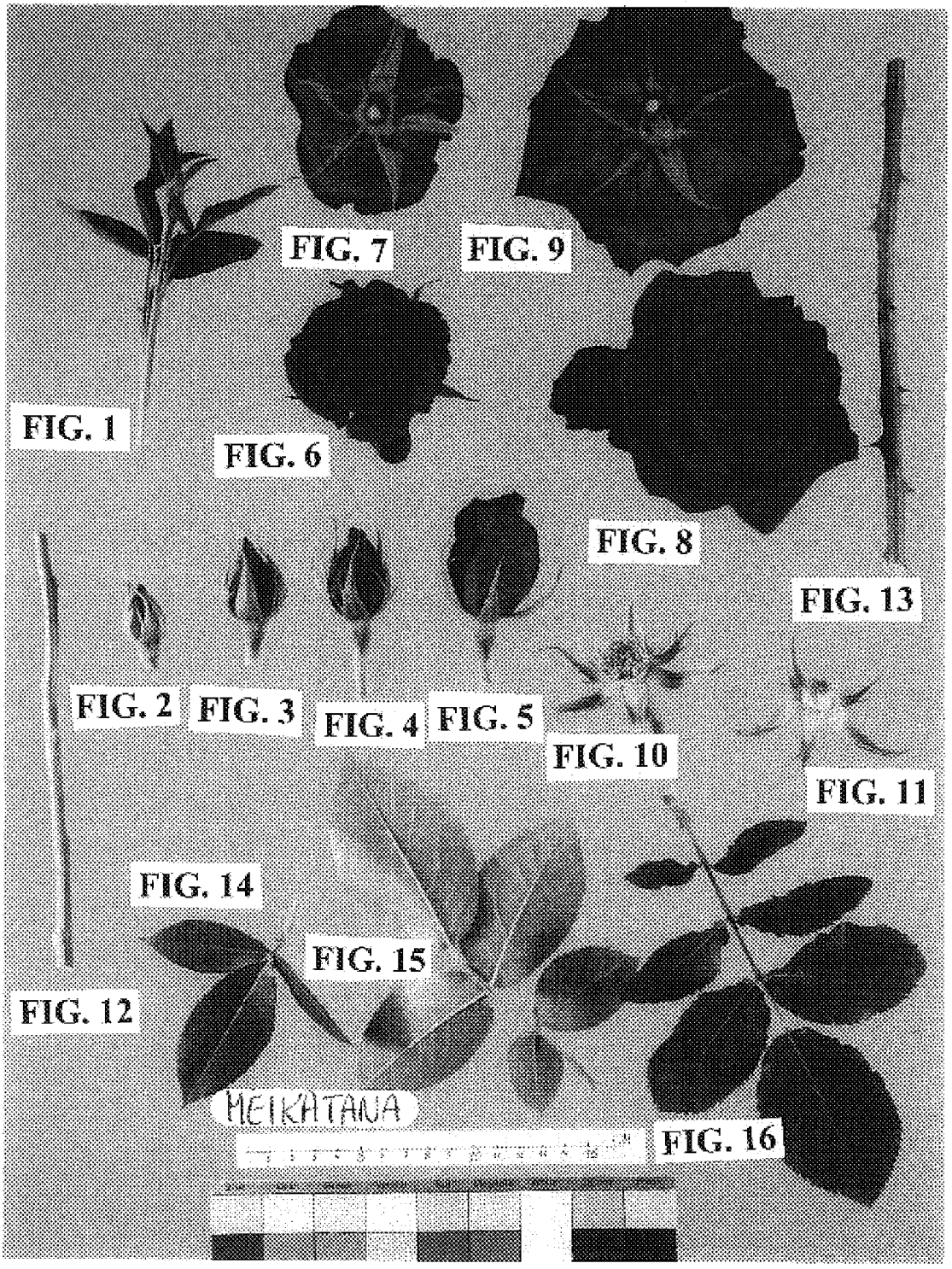

Botanical/commercial classification: *Rosa hybrida*/Hybrid Tea rose plant.
Varietal denomination: cv. Meikatana

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) was the product of the cross of the 'Meibeka' variety (non-patented in the United States) and the 'Meigormon' variety( U.S. Plant Pat. No. 8,647). The male parent (i.e., the pollen parent) was the 'Tankalcig' variety (U.S. Plant Pat. No. 10,650). The 'Tankalcig' variety is marketed under the BLACK MAGIC trademark. The parentage of the new variety is summarized as follows:

('Meibeka'×'Meigormon')×'Tankalcig'.

The seeds resulting from the above pollination were sown and small plants were obtained which were physically and biologically different from each other. Selective study resulted in the identification of a single plant of the new variety.

It was found that the new Hybrid Tea rose plant of the present invention:

(a) forms in abundance on a nearly continuous basis attractive large double very velvety blossoms that are dark red in coloration, (b) displays rather dense glossy green foliage, (c) develops well on its own roots, and (d) is particularly well suited for cut flower production under greenhouse growing conditions.

The attractive dark red blossoms tend to be regular in appearance. The new variety performs well under greenhouse growing conditions during the production of cut flowers.

The new variety can be readily distinguished from its ancestors. For instance, the blossom coloration of the 'Meibeka' variety is salmon, the 'Meigormon' variety forms smaller blossoms, and the 'Tankalcig' variety bears considerably more prickles on adult wood.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another.

The new variety has been named 'Meikatana'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately 1½ years of age and were observed during October while growing on *Rosa indica* understock outdoors at Le Cannet des Maures, Var, France. Dimensions in centimeters and a standard color presentation are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of 1½ year old plants during October while budded on *Rosa indica* understock and growing in greenhouses at Le Cannet des Maures, Var, France.

Class: Hybrid Tea.

Plant:

*Height*.—When pruned to a height of 0.85 cm, floral stems having lengths of approximately 80 to 90 cm commonly are produced.

*Width*.—Commonly approximately 70 to 100 cm on average.

Branches:

*Color*.—Young stems: near Yellow-Green Group 146B. Adult wood: near Yellow-Green Group 146A.

*Thorns*.—On young stems: Small prickles: Quantity: none. Long prickles: Quantity: none. On adult stems: Small prickles: Quantity: none. Long prickles: Configuration: substantially straight and longish pointed on the upper surface and slightly concave on the under surface with a narrow and short base. Quantity: approximately 8 on average on a stem length of 10 cm. Length: approximately 0.6 mm on average. Color: near Yellow-Green Group 151A.

Leaves:

*Stipules*.—Smooth, adnate, pectinate, narrow, approximately 1.4 cm in length on average, approximately 0.4 cm in width on average, Yellow-Green Group 146B on the upper surface, and Yellow-Green Group 146D on the under surface.

*Petioles*.—Upper surface: near Yellow-Green Group 146B in coloration. Under surface: near Yellow-Green Group 147C in coloration. Texture: smooth and without prickles. Length: approximately 3.2 cm for the terminal leaflet.

*Rachis*.—Upper surface: near Yellow-Green Group 146B in coloration. Under surface: near Yellow-Green Group 147D in coloration. Texture: smooth.

*Leaflets*.—Number. 3, 5, and 7 (most often). Shape: generally elliptical with a pointed somewhat cuspidate tip and a rounded obtuse base. Size: the terminal leaflets commonly are approximately 8.7 cm in length and approximately 4.6 cm in width on average. Serration: small and single (as illustrated). Texture: somewhat flexible. General appearance: glossy and rather dense. Color (young foliage): Upper surface: near Green Group 137B. Under surface: near Yellow-Green Group 146B. Color (adult foliage): Upper surface: near Green Group 139A. Under surface: near Yellow-Green Group 147B.

Inflorescence:

*Number of flowers*.—Commonly one blossom per stem.

*Peduncle*.—Pubescent, approximately 8 cm in length on average, approximately 0.5 cm in diameter on average, and near Green Group 143C in coloration.

*Sepals*.—Upper surface: tomentose and near Green Group 138B in coloration. Under surface: tomentose and near Yellow-Green Group 144B in coloration. Size: near 4.6 cm in length on average, and near 1 cm in width at the widest point on average. Configuration: longish pointed and narrow at the base. Extensions: two sepals commonly possess no extensions and three sepals commonly possess weak extensions.

*Buds*.—Shape: conical. Size: large. Length: approximately 4 cm on average. Width: near 3 cm on average at the widest point. Color: Upper surface: near Red Group 46A. Under surface: near Red Group 53B.

*Flower*.—Shape: cup-shaped. Diameter: approximately 10.6 cm on average. Color (in the course of opening): Upper surface: velvety red, near Red Group 46A. Under surface: near Red Group 53A. Color (when fully open): Upper surface: velvety red, near Red Group 46A. Under surface: near Red Group 53A. Color stability: substantially no discoloration. Fragrance: none. Lasting quality: the blossoms commonly last approximately 13 to 15 days on the plant on average, and approximately 12 to 14 days on average when cut and placed in a vase. Petal number: approximately 36 on average under normal growing conditions. Petal shape: with a substantially rounded tip and base. Petal texture: consistent and somewhat firm. Petal length: approximately 5.9 cm on average. Petal width: approximately 6 cm on average. Petal arrangement: imbricated; and with some petaloids. Petal drop: good with the petals commonly detaching cleanly before drying. Stamen number: approximately 82 on average. Anthers: regularly arranged around the styles, approximately 0.4 cm in size on average, and near Yellow-Orange Group 22A in coloration. Pollen: present. Filaments: approximately 1 cm in length on average and near Red Group 42A in coloration. Pistils: approximately 117 on average. Stigmas: approximately 0.2 cm in size on average and near Red Group 42B in coloration. Styles: approximately 0.7 cm in length on average, and near Yellow Group 13C in coloration. Receptacle: smooth, funnel-shaped in longitudinal section, approximately 1 cm in length and width on average, and near Yellow-Green Group 144A in coloration. Hips: none observed during greenhouse growing conditions to date.

Development:

*Vegetation*.—Very strong.

*Blooming*.—Precocious, very abundant and nearly continuous.

*Tolerance to diseases*.—No disease problem has been observed to date under greenhouse growing conditions.

*Aptitude to forcing*.—Excellent.

I claim:

1. A new and distinct Hybrid Tea rose plant characterized by the following characteristics:

(a) forms in abundance on a nearly continuous basis attractive large double very velvety blossoms that are dark red in coloration, (b) displays rather dense glossy green foliage, (c) develops well on its own roots, and (d) is particularly well suited for cut flower production under greenhouse growing conditions;

substantially as herein shown and described.

* * * * *

MEIKATANA